US010561648B2

(12) United States Patent
Hall et al.

(10) Patent No.: US 10,561,648 B2
(45) Date of Patent: Feb. 18, 2020

(54) INHIBITION AND TREATMENT OF BACTERIAL INFECTIONS BY SEX-SPECIFIC GPER TARGETING (71) Applicant: STC.UNM, Albuquerque, NM (US)

(72) Inventors: Pamela Hall, Albuquerque, NM (US); Eric R. Prossnitz, Albuquerque, NM (US); Helen J. Hathaway, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 16/067,721

(22) PCT Filed: Jan. 9, 2017

(86) PCT No.: PCT/US2017/012687
§ 371 (c)(1),
(2) Date: Jul. 2, 2018

(87) PCT Pub. No.: WO2017/123492
PCT Pub. Date: Jul. 20, 2017

(65) Prior Publication Data
US 2019/0000830 A1 Jan. 3, 2019

Related U.S. Application Data (60) Provisional application No. 62/277,125, filed on Jan. 11, 2016.

(51) Int. Cl.
| A61K 31/473 | (2006.01) |
| A61K 45/06 | (2006.01) |
| A61K 35/644 | (2015.01) |
| A61K 38/14 | (2006.01) |
| C07K 14/705 | (2006.01) |
| A61K 31/4741 | (2006.01) |
| A61P 31/04 | (2006.01) |

(52) U.S. Cl.
CPC ........ *A61K 31/473* (2013.01); *A61K 31/4741* (2013.01); *A61K 35/644* (2013.01); *A61K 38/14* (2013.01); *A61K 45/06* (2013.01); *A61P 31/04* (2018.01); *C07K 14/70567* (2013.01)

(58) Field of Classification Search
CPC .................................................. A61K 31/473
USPC ....................................................... 514/290
See application file for complete search history.

(56) References Cited

U.S. PATENT DOCUMENTS 5,840,684 A * 11/1998 Cooper ................. C07K 9/008
514/2.4
8,487,100 B2 7/2013 Prossnitz et al.

FOREIGN PATENT DOCUMENTS

WO 2012122101 A1 9/2012

OTHER PUBLICATIONS

Seto K, et al.; Non-genomic oestrogen receptor signal in B lymphocytes: an approach towards therapeutic interventions for infection, autoimmunity and cancer. The International Journal of Biochemistry & Cell Biology 2016; vol. 76, nr. 115, pp. 115-118.
Corriden R, et al.; Tamoxifen augments the innate immune function of neutrophyls through modulation of intracellular ceramide. Nature Communications Oct. 13, 2014; 6:8369. DOI: 10.1038/ ncomm9369.
Triplett KD, et al.; GPER activation protects against epithelial barrier disruption by *Staqphylococcus aureus* alpha-toxin. Scientific Reports Feb. 4, 20109; vol. 9, pp. 1343. doi:1038/S41598-018-37951-3.
Malachowa N, Kobayashi SD, Braughton KR, DeLeo FR. Mouse model of *Staphylococcus aureus* skin infection. Methods Mol Biol. 2013;1031:109-16. doi: 10.1007/978-1-62703-481-4_14. PubMed PMID: 23824894.
Bologa CG, Revankar CM, Young SM, Edwards BS, Arterburn JB, Kiselyov AS, Parker MA, Tkachenko SE, Savchuck NP, Sklar LA, Oprea TI, Prossnitz ER. Virtual and biomolecular screening converge on a selective agonist for GPR30. Nat Chem Biol. 2006;2(4):207-12. doi: 10.1038/nchembio775. PubMed PMID: 16520733.
Public health dispatch: outbreaks of community-associated methicillin-resistant *Staphylococcus aureus* skin infections—Los Angeles County, California, 2002-2003. Can Commun Dis Rep. 2003;29(12):110-2. Epub Jun. 26, 2003. PubMed PMID: 12822295.
Kennedy AD, Bubeck Wardenburg J, Gardner DJ, Long D, Whitney AR, Braughton KR, Schneewind O, DeLeo FR. Targeting of alpha-hemolysin by active or passive immunization decreases severity of USA300 skin infection in a mouse model. J Infect Dis. 2010;202(7):1050-8. doi: 10.1086/656043. PubMed PMID: 20726702; PMCID: 2945289.
Berube BJ, Wardenburg JB. *Staphylococcus aureus* alpha-Toxin: Nearly a Century of Intrigue. Toxins (Basel). 2013;5(6):1140-66. doi: DOI 10.3390/toxins5061140. PubMed PMID: WOS:000320770400006.
Cramer et al.; Oral Administration of the Broad-Spectrum Antibiofilm Compound Toremifene Inhibits Canida albicans and *Staphylococcus aureus* Biofilm Formation In Vitro. Antimicrobial Agents and Chemotherapy Oct. 6, 2014; vol. 58, pp. 7606-7610.
Dennis et al.; Identification of a GPER/GPR30 antagonist with improved estrogen receptor counterselectivity. The Journal of Steroid Biochemistry and Molecular Biology Jul. 14, 2011; vol. 127, pp. 358-366.

* cited by examiner

*Primary Examiner* — Kevin E Weddington
(74) *Attorney, Agent, or Firm* — Henry D. Colemam; R. Neil Sudol (57) ABSTRACT

The present invention is directed to the use of compounds which are modulators of the G protein-Coupled Estrogen Receptor (GPER) for the inhibition —and/or treatment of Bacterial infections, especially including metMctHin-resistant *Staphylococcus aureus* (MRSA) infections. Pharmaceutical compositions and methods of treatment of bacterial pathogens, including MRSA are also described.

13 Claims, 8 Drawing Sheets

INHIBITION AND TREATMENT OF BACTERIAL INFECTIONS BY SEX-SPECIFIC GPER TARGETING

RELATED APPLICATIONS

This application is a United States national phase patent application based upon international patent application number PCT/US2017/012687 of international filing date 9 Jan. 2017, which claims the benefit of priority from United States provisional application U.S. 62/277,125, filed 11 Jan. 2016 of identical title, the entire contents of which said two applications are incorporated by reference herein.

GRANT SUPPORT

This invention was made with government support under grant no. AI091917 awarded by National Institutes of Health (NIH). The government has certain rights in the invention.

FIELD OF THE INVENTION

The present invention is directed to the use of compounds which are modulators of the G protein-Coupled Estrogen Receptor (GPER) for the inhibition and/or treatment of Bacterial infections, especially including *Staphylococcus aureus* and methicillin-resistant *Staphylococcus aureus* (MRSA) infections.

Background and Overview of the Invention

*Staphylococcus aureus* is a gram-positive bacterium well known for human infections. Some forms of this infection can progress in patients to pneumonia and bloodborne infections. These conditions are quite serious and sometimes can to cause fatality. Historically, with the initial introduction of penicillin and penicillin-like antibiotics, successful treatments were found for *S. aureus* infections. However, some time ago, because of the development of resistance to penicillin antibiotics by *S. aureus*, the anti-staphylococcal penicillins Methicillin, Nafcillin and Oxacillin were introduced. However, infections caused by *S. aureus* strains resistant to these anti-staphylococcal penicillins, jointly named methicillin-resistant *S. aureus* (MRSA), began to appear thereafter. Resistance renders these infections far more difficult to treat with standard antibiotics and recently the search has become intensive for finding agents useful to resolve these infections. MRSA poses a serious health problem, especially in hospitals, nursing homes and other facilities, but also in numerous public settings. The risks of MRSA are particularly significant in people who are immunocompromised (for example, those with HIV/AIDS) or have immune systems that are weakened (for example, those with diabetes or cancer). MRSA causes a range of diseases from skin and wound infections to pneumonia and bloodstream infections that can cause sepsis and death and significant research is ongoing to find agents which can inhibit or treat these infections. Female mice are better protected against many bacterial infections compared to males. We have identified the G protein-Coupled Estrogen Receptor (GPER) as a prophylactic and therapeutic target to enhance the host immune response to bacterial infection. Proof of principle has been demonstrated in vivo in a mouse model of methicillin-resistant *Staphylococcus aureus* (MRSA) skin infection. Treatment of male and female mice with the GPER agonist G-1 significantly reduces the pathogenesis of infection and promotes bacterial clearance. Targeting the host immune response using GPER agonists and antagonists (G-1, G15, G36) will provide protection against and treatment for infections caused by many human pathogens.

BRIEF DESCRIPTION OF THE FIGURES

FIG. 3 shows that GPER activation promotes protection against SA SSTI in male mice. WT (C57BL/6) male mice were treated i.p. with vehicle or 200 ng G-1 on days −2, −1, 0, +1 and +2 relative to subcutaneous infection with $1.8 \times 10^7$ CFU of USA300 MRSA isolate LAC. Mice were weighed and abscess and dermonecrosis size measured daily before mice were sacrificed on day 3 or day 7 post-infection. Daily measures (mean±sem) and calculated area under the curve (AUC) values (median and $5^{th}$ to $95^{th}$ percentile range) for the 3-day infection showing differences in (A) abscess area, (B) dermonecrosis and (C) percent weight loss, and well as (D) day 3 post-infection bacterial burden at the site of infection. Dermonecrosis was measured daily in mice treated as above with vehicle or G-1. Mann-Whitney test, n=7 mice per group from two independent experiments. *$p<0.05$; **$p<0.01$.

FIG. 7 shows that GPER activation promotes protection against SA SSTI in female mice. WT (C57BL/6) female mice were treated i.p. with vehicle or 200 ng G-1 on days −2, −1, 0, +1 and +2 relative to subcutaneous infection with $2.3 \times 10^7$ CFU of USA300 MRSA isolate LAC. Mice were weighed and abscess and dermonecrosis size measured daily before mice were sacrificed on day 3 post-infection. Daily measures (mean t sem) and calculated area under the curve (AUC) values (median and $5^{th}$ to $95^{th}$ percentile range) for the 3-day infection showing differences in (A) abscess area, (B) dermonecrosis and (C) percent weight loss, and well as (D) day 3 post-infection bacterial burden at the site of infection. Mann-Whitney test, n=7-8 mice per group from two independent experiments. ns, not significant; **p<0.01.

BRIEF DESCRIPTION OF THE INVENTION

The present invention is directed to compounds that are modulators (i.e. agonists or inhibitors) of GPER and as such are useful in the inhibition, reducing the likelihood and/or treatment of bacterial infections including MRSA infections. The present invention is thus directed to compounds and methods which are useful to treat bacterial infections, especially *Staphylococcus aureus* infections, and in particular, drug/antibiotic resistant *Staphylococcus aureus* (MRSA) and secondary disease states and conditions related to same. Compounds according to the present invention are shown to reduce the pathogenesis of MRSA infections and promote bacterial clearance. GPER agonists, especially including compound G-1 are shown to have a favorable effect on MRSA pathogenesis and bacterial clearance.

The present invention relates to compounds and their use in the treatment of bacterial infections, especially MRSA infections in both male and female patients.

The present invention also relates to a method of treating MRSA comprising administering to a patient an effective amount of a GPER modulator, alone or in combination with at least one additional anti-MRSA compound as described herein.

Preferred compounds useful in the present invention are according to the chemical structure I:

Where X is =N—, O, S, or N—R, with the proviso that when X is N—R and R is a bond, N together with R$^1$ forms a 5- to 7-membered optionally substituted heterocyclic group;

R is a bond, H, OH, NO$_2$, an optionally substituted C$_1$-C$_6$ hydrocarbyl, preferably an optionally substituted alkyl, an optionally substituted aryl, an optionally substituted heteroaryl, an optionally substituted heterocycle, an optionally substituted —C(O)—(C$_1$-C$_6$) alkyl (amide), an optionally substituted —C(O)—O—(C$_1$-C$_6$) alkyl (urethane), an optionally substituted —C(O)—NH(C$_1$-C$_6$) alkyl (urea), an optionally substituted —C(O)—N(C$_1$-C$_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle);

R$^1$, R$^2$ and R$^5$ are each independently selected from H, OH, NO$_2$, halogen (F, Br, Cl or I), a C$_1$-C$_6$ optionally substituted carboxylic acid group, an optionally substituted O—(C$_1$-C$_6$)alkyl, optionally substituted C$_1$-C$_6$ hydrocarbyl, an optionally substituted aryl, an optionally substituted heteroaryl, an optionally substituted heterocycle, an optionally substituted —C(O)—(C$_1$-C$_6$) alkyl (ketone), an optionally substituted —C(O)—O—(C$_1$-C$_6$) alkyl (ester), an optionally substituted O—C(O)—(C$_1$-C$_6$) alkyl (ester), an optionally substituted —C(O)—NH(C$_1$-C$_6$) alkyl (urea), an optionally substituted —C(O)—N(C$_1$-C$_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle);

R$^3$ and R$^4$ are each independently selected from H, OH, NO$_2$, halogen (F, Br, Cl or I), a C$_1$-C$_6$ optionally substituted carboxylic acid group, an optionally substituted O—(C$_1$-C$_6$) alkyl, an optionally substituted C$_1$-C$_6$ hydrocarbyl, an optionally substituted aryl, an optionally substituted heteroaryl, an optionally substituted heterocycle, an optionally substituted —C(O)—(C$_1$-C$_6$) alkyl (ketone), an optionally substituted —C(O)—O—(C$_1$-C$_6$) alkyl (ester), an optionally substituted O—C(O)—(C$_1$-C$_6$) alkyl (ester), an optionally substituted —C(O)—NH(C$_1$-C$_6$) alkyl (urea), an optionally substituted —C(O)—N(C$_1$-C$_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl) or R$^3$ and R$^4$ together form a 5- or 6-membered optionally substituted carbocyclic (which may be saturated or unsaturated), optionally substituted aryl, optionally substituted heteroaryl or optionally substituted heterocyclic group;

R$^6$ and R$^7$ are each independently absent or are selected from H, OH, NO$_2$, halogen (F, Br, Cl or I), a C$_1$-C$_6$ optionally substituted carboxylic acid group, an optionally substituted O—(C$_1$-C$_6$)alkyl, an optionally substituted C$_1$-C$_6$ hydrocarbyl, an optionally substituted aryl, an optionally substituted heteroaryl, an optionally substituted heterocycle, an optionally substituted —C(O)—(C$_1$-C$_6$) alkyl (ketone), an optionally substituted —C(O)—O—(C$_1$-C$_6$) alkyl (ester), an optionally substituted O—C(O)—(C$_1$-C$_6$) alkyl (ester), an optionally substituted —C(O)—NH(C$_1$-C$_6$) alkyl (urea), an optionally substituted —C(O)—N(C$_1$-C$_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl), or together R$^6$ and R$^7$ form a 4-, 5-, 6- or 7-membered optionally substituted carbocyclic (which may be saturated or unsaturated), an optionally substituted aryl, optionally substituted heteroaryl or optionally substituted heterocyclic group, or a 5- to 9-membered optionally substituted carbocyclic or heterocyclic bicyclic group, with the proviso that R$^7$ is not absent when both R$^{7'}$ and R$^{7''}$ are also absent;

$R^{6'}$ is absent, H, a $C_1$-$C_6$ optionally substituted hydrocarbyl group (preferably H, $CH_3$ or $CH_2CH_3$) or together with $R^6$ forms a =O group;

$R^{7'}$ is absent, H, optionally substituted hydrocarbyl group (preferably H, $CH_3$ or $CH_2CH_3$), or together with $R^7$ forms a =O group;

$R^{7''}$ is absent, H, OH, halogen (F, Br, Cl or I), an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl);

$R^{8'}$ is absent (when the carbon to which $R^{8'}$ is attached and the carbon to which $R^6$ is attached form an optional double bond), H, $CH_3$ or $CH_2CH_3$;

$R^{10}$, $R^{11}$, $R^{12}$ and $R^{13}$ are each independently H, OH, $NO_2$, halogen (F, Br, Cl or I), a $C_1$-$C_6$ optionally substituted carboxylic acid group, an optionally substituted O—($C_1$-$C_6$)alkyl, an optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheteroaryl);

$R^{14}$ is H, OH, $NO_2$, halogen (F, Br, Cl or I), a $C_1$-$C_6$ optionally substituted carboxylic acid group, an optionally substituted O—($C_1$-$C_6$)alkyl, optionally substituted $C_1$-$C_6$ hydrocarbyl, an optionally substituted aryl, an optionally substituted heteroaryl, an optionally substituted heterocycle, an optionally substituted —C(O)—($C_1$-$C_6$) alkyl (ketone), an optionally substituted —C(O)—O—($C_1$-$C_6$) alkyl (ester), an optionally substituted O—C(O)—($C_1$-$C_6$) alkyl (ester), an optionally substituted —C(O)—NH($C_1$-$C_6$) alkyl (urea), an optionally substituted —C(O)—N($C_1$-$C_6$)dialkyl, an optionally substituted —C(O)—NH(aryl), an optionally substituted —C(O)—N(diaryl), an optionally substituted —C(O)—NH(heteroaryl), an optionally substituted —C(O)—N(diheteroaryl), an optionally substituted —C(O)—NH(heterocycle) or an optionally substituted —C(O)—N(diheterocycle) or together with the carbon to which $R^7$ is attached forms a 5-, 6- or 7-membered optionally substituted carbocyclic (which may be saturated or unsaturated), optionally substituted aryl, optionally substituted heteroaryl or optionally substituted heterocyclic ring; or a stereoisomer, pharmaceutically acceptable salt, solvate, or polymorph thereof. These compounds are disclosed in U.S. Pat. No. 7,875,721, the entire contents of which is incorporated by reference herein.

Preferred compounds according to the present invention relate to compounds according to the chemical structure II:

Where R, $R^1$, $R^2$, $R^3$, $R^4$, $R^5$, $R^{8'}$, $R^{10}$, $R^{11}$, $R^{12}$ and $R^{13}$ are as previously described above, or a stereoisomer, pharmaceutically acceptable salt, solvate, or polymorph thereof. In preferred aspects of the invention, R8' is H and the two carbons of the five membered ring shared by the piperidine ring are saturated.

Preferred compounds according to the present invention also relate to compounds according to the chemical structure III:

Where R, $R^1$, $R^2$, $R^3$, $R^4$, $R^5$, $R^{8'}$, $R^{10}$, $R^{11}$, $R^{12}$ and $R^{13}$ are as previously described above;

Y is an optionally substituted $(CH_2)_n$ group where n is 0, 1 or 2, an optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle; or a stereoisomer, pharmaceutically acceptable salt, solvate, or polymorph thereof;

Z is an optionally substituted $(CH_2)$, group where n is 1 or 2, an optionally substituted =CH— group, a C=O group, O, S, optionally substituted N—($C_1$-$C_6$)alkyl, optionally substituted N-aryl, optionally substituted N-heteroaryl, optionally substituted N-heterocycle, optionally substituted N—C(O)—($C_1$-$C_6$)alkyl, optionally substituted N—C(O)-aryl, optionally substituted N—C(O)-heteroaryl, optionally substituted N—C(O)-heterocycle; or a stereoisomer, pharmaceutically acceptable salt, solvate or polymorph thereof.

In preferred aspects of the invention, $R^3$ and $R^4$ form a five membered heterocyclic ring, preferably having two heteroatoms. Preferably, $R^3$ and $R^4$ form a furan ring. In preferred aspects of the invention, R is H or a $C_1$-$C_3$ alkyl group. In preferred embodiments according to the present invention, at least one of $R^1$, $R^2$, $R^5$, $R^{10}$, $R^{11}$, $R^{12}$ and $R^{13}$ and as many as three of these substituents is a halogen group. In certain preferred embodiments one of these $R^1$, $R^2$, $R^5$, $R^{10}$, $R^{11}$, $R^{12}$ and $R^{13}$, groups is a $(CH_2)_n$—$NH_2$ group, where n is 1-6, preferably 1, 2 or 3, preferably 2, where the amino group can be further reacted to provide a fluorescent label. In certain preferred embodiments, $R^1$, $R^2$ or $R^5$ is a halogen (preferably F or Br) or an optionally substituted $C_1$-$C_6$ hydrocarbyl group (alkyl or a $C_2$-$C_6$ alkenyl or alkynyl) or a —O—($C_1$-$C_6$ alkyl) group and $R^{11}$ or $R^{12}$ is a halogen, a $C_2$-$C_6$ acyl group (preferably, acetyl), a carboxyl acid group, an optionally substituted (with at least one $C_1$-$C_3$ alkyl group) carboxamido group, a —O—($C_1$-$C_6$ alkyl) group or an optionally substituted ester group (—C(O)O—($C_1$—C(alkyl) or —O—C(O)—($C_1$-$C_6$ alkyl)).

A preferred compound for use in the present invention is a compound according to the following structure.

Where R is acetyl, H or an isopropyl group, or an isomer, diastereomer, enantiomer, or pharmaceutically acceptable salt, solvate or polymorph thereof.

Figure 3:
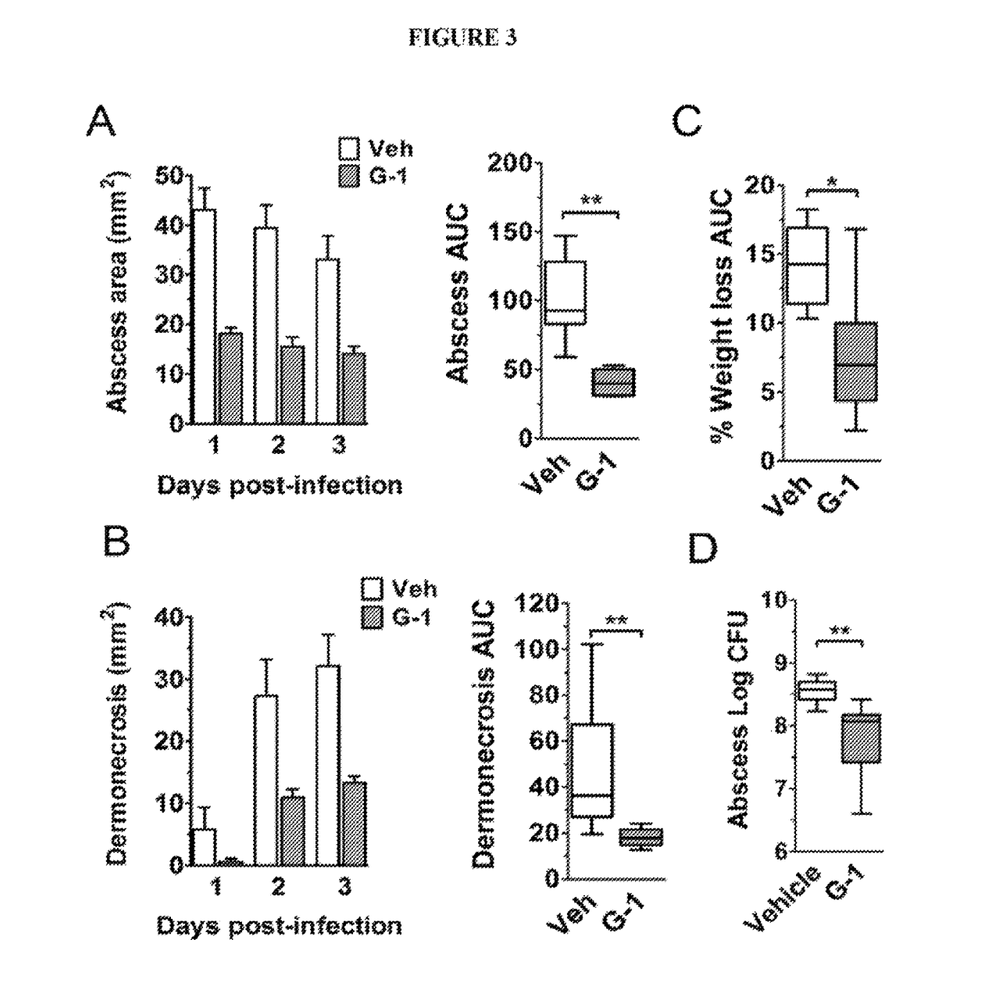
Figure 4:
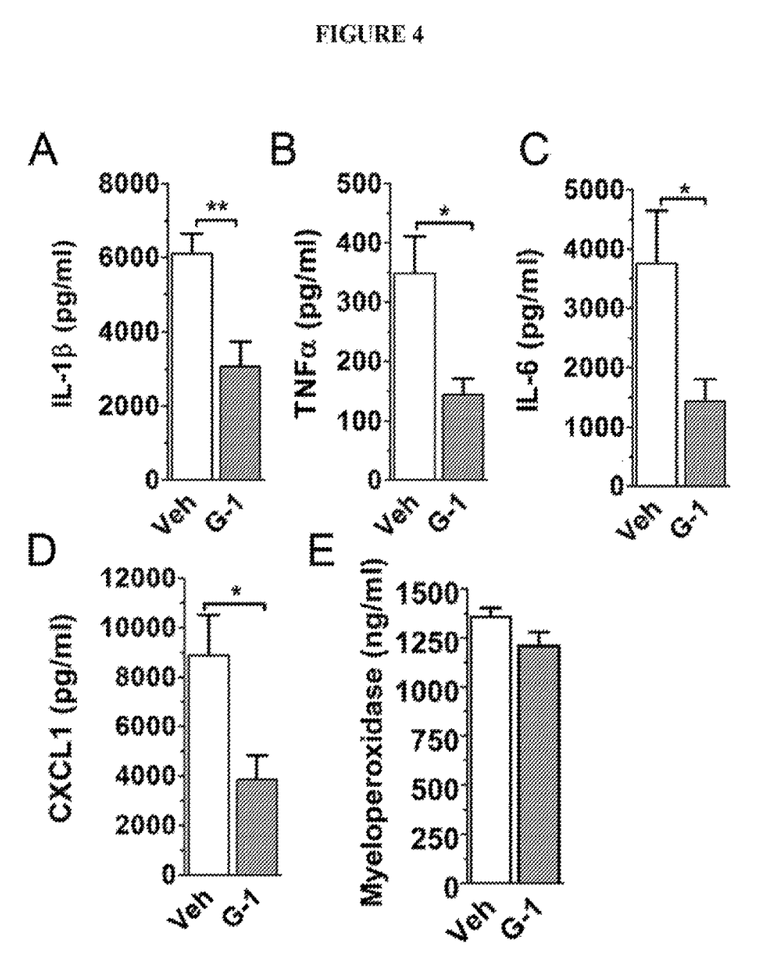
FIG. 4 shows that GPER activation is accompanied by reduced inflammation during SA SSTI. WT (C57BL/6) male mice were treated i.p. with vehicle or 200 ng G-L on days −2, −1, 0, +1 and +2 relative to subcutaneous infection with $1.8 \times 10^7$ CFU of USA300 MRSA isolate LAC. (A) IL-1β, (B) TNFα, (C) IL-6, (D) CXCL1 and (E) myeloperoxidase levels measured in clarified infection site homogenate collected on day 3 post-infection. Data are mean±sem from n=7 mice per group from two independent experiments. *$p<0.05$; **$p<0.01$.

Even more preferred compounds are

Where R is an acetyl group (agonist compound G-1), H (antagonist compound G15) or an isopropyl group (antagonist compound G36), or a pharmaceutically acceptable salt thereof. These compounds are shown in FIG. 3.

The above compounds are known in the art as GPR30/GPER modulators (agonists or inhibitors). It has unexpectedly been discovered that the modulation of GPR30/GPER has an unexpected favorable impact (modulation) on *Staphylococcus aureus*, especially MRSA infection. Thus, modulators of GPR30/GPER as described herein represent a previously unknown therapeutic option for the treatment of *Staphylococcus aureus*, especially including MRSA infection.

Additional GPR30/GPER modulators for use in the present invention include selective estrogen receptor modulators (SERMS), including bazedoxifene (Duavee), broparestrol (Acnestrol), clomifene (Clomid), cyclofenil (Sexovid), lasofoxifene (Fablyn), ormeloxifene (Centron, Sevista), ospemifene (Osphena), raloxifene (Evista), tamoxifen (novaldex) and toremifene (Farseton), as well as acolbifene (4-hydroxytamoxifen), arzoxifene, brilanestrant, clomifenoxide (clomifene N-oxide), droloxifene (3-hydroxytamoxifen), elascestrant, endomifene, 4-hydroxyetacstil (GW-7604), miproxifene, nafbxidine, nitromifene (CI-628), panomifene, pipendoxifene, tesmilifene, trioxifene, zindoxifene (D-16726), zuclomifene; selective estrogen receptor degraders or downregulators (SERDS), including ICI182, 780/faslodex/Fulvestrant; and pytoestrogens or animal estrogens, including the isoflavones, for example, genistein, formonetin, daidzein and blochanin A, coumestans, including coumestrol, 4'-methoxycoumestrol, repensol and trifoliol or the estrogen 17-β-estradiol, or mixtures thereof.

The present invention also relates to pharmaceutical compositions comprising an effective amount of one or more of the above-referenced GPR30/GPER modulator compounds, optionally in combination with a pharmaceutically acceptable additive, carrier or excipient and further optionally in combination with at least one additional bioactive agent, preferably a drug which also treats bacterial pathogens, especially *Staphylococcus aureus*, including MRSA (e.g. an additional anti-MRSA agent as described herein).

A method of treating *Staphylococcus aureus*, especially MRSA in a patient in need comprises administering an effective amount of at least GPER modulator to said patient alone or optionally in combination with at least one additional bioactive agent, preferably an agent that also may be used to treat *Staphylococcus aureus*, especially including MRSA (an additional anti-MRSA agent). In particular aspects, a method of treating *Staphylococcus aureus*, especially MRSA in a patient in need comprises administering an effective amount of at least one GPER modulator (e.g., compound G-1, G15 and/or G36) alone, optionally in combination with a pharmaceutically acceptable carrier, additive or excipient, and/or further optionally in combination with at least one additional bioactive agent, preferably an agent that also may be used to treat bacterial pathogens, especially *Staphylococcus aureus*, including MRSA (an additional anti-MRSA agent).

DETAILED DESCRIPTION OF THE INVENTION

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "patient" or "subject" refers to a mammal, preferably a human, but includes especially a domesticated animal, for example, a dog, cat, cow, horse, sheep, pig, especially a dog or a cat, in need of treatment or therapy to which compounds according to the present invention are administered in order to treat a bacterial pathogen, including *Staphylococcus aureus*, especially MRSA. Where a gender of a patient is indicated that gender is either a female or a male. In preferred aspects the patient is a male human or a female human.

The term "effective" is used to describe an amount, concentration an/or duration of a compound or component which produces an intended effect by use of that compound or component in a manner consistent with that intended effect, whether the effect is a favorable treatment, a cure, an amelioration of symptoms, the production of a compound, etc.

The term "GPR30 receptor" refers to a 7-transmembrane G protein-coupled receptor that mediate estrogen-dependent signal transduction. GPR30 is an intracellular protein, found in the endoplasmic reticulum, which binds estrogen with high affinity ($K_4$~6 nM) and mediates rapid cellular responses including calcium mobilization and phosphatidylinositol 3,4,5 trisphosphate production in the nucleus. GPR30 receptor refers to all types of GPR30 receptor, regardless of the tissue in which such receptor is found and refers to any variant thereof, including receptors of mammals (preferably, humans and domesticated mammals where veterinary applications are relevant) and variants thereof. Other names which have been used for GPR30 include GPER, GPER-1, CMKRL2, DRY 12, FEG-1, GPCR-Br, LERGU, LERGU2, LyGPR, CEPR and MGC99678, among others.

The term "modulate" means, with respect to disease states or conditions mediated by binding of a compound according to the present invention to GPR30 and/or GPER to produce, either directly or indirectly, an improvement or lessening of a condition or disease state which was, prior to administration of a compound according to the present invention, sub-optimal and in many cases, debilitating and even life threatening. Modulation may occur by virtue of agonist activity, antagonist activity or mixed agonist/antagonist activity (depending on the receptor site).

The term "compound", "GPER modulator", "GPER agonist" or "GPER inhibitor", as used herein, unless otherwise indicated, refers to any specific chemical compound disclosed herein which is a modulator (i.e. an agonist or inhibitor) of GPER and includes in context, tautomers, regioisomers (especially cis/trans), geometric isomers, and where applicable, optical isomers thereof, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., cis and trans isomers) and all optical isomers of the present compounds (eg., R and S enantiomers), as well as racemic, diastereomeric and/or other mixtures of such isomers, as well as all pharmaceutically acceptable salt forms, solvates, polymorphs and prodrug forms of the present compounds, where applicable.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The terms "treat", "treating", and "treatment", etc., as used herein within context, also refers to any action providing a benefit to a patient at risk for any of the disease states or conditions (bacterial pathogens, especially MRSA infections) which can be treated pursuant to the present invention (e.g., inhibit, reduce the severity, cure, etc.). Treatment, as used herein, principally encompasses therapeutic treatment, but may also encompass both prophylactic and therapeutic treatment, depending on the context of the treatment. The term "prophylactic" when used in context, means to reduce the likelihood of an occurrence or in some cases, reduce the severity of an occurrence within the context of the treatment of a disease state or condition otherwise described herein.

The term "prevention" is used within context to mean "reducing the likelihood" of a condition or disease state from occurring as a consequence of administration or concurrent administration of one or more compounds or compositions according to the present invention, alone or in combination with another agent. Thus, the term prevention is used within the context of a qualitative measure and it is understood that the use of a compound according to the present invention to reduce the likelihood of an occurrence of a condition or disease state as otherwise described herein will not be absolute, but will reflect the ability of the compound to reduce the likelihood of the occurrence within a population of patients or subjects in need of such prevention.

The term "MRSA" as used herein describes any strain of *Staphylococcus aureus* that has antibiotic resistance, including resistance to methicillin, nafcillin, oxacillin. *Staphylococcaures aureus* (*S. aureus*) is a gram-positive bacterium that is frequently found in the human respiratory tract and on the human skin. Although *S. aureus* is not usually pathogenic, it is known to cause skin infections (e.g., boils), respiratory disease (e.g., pneumonia), bloodstream infections, bone infections (osteomyelitis), endocarditis and food poisoning. The bacterial strains that often produce infections generate protein toxins and also express cell-surface proteins that apparently bind and inactivate antibodies. MRSA is responsible for a number of very difficult-to-treat infections in humans. The resistance does render MRSA infections far more difficult to treat. MRSA is often labeled as being community acquired MRSA ("CA-MRSA") and hospital acquired MRSA ("HA-MRSA"). MSSA (methicillin sensitive *Staphylococcus aureus*) refers to a strain of *Staphylococcus aureus* that exhibits sensitivity to methicillin.

The term "coadministration" or "combination therapy" is used to describe a therapy in which at least two active compounds in effective amounts are used to treat MRSA or MSSA and another disease state or condition at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more bioactive agents, including antiviral agents, anticancer agents (especially anticancer agents where a *Staphylococcus aureus* infection, especially including MRSA is found), and agents which may otherwise be used to treat disease states and conditions often found in combination with *Staphylococcus aureus*, especially MRSA infections. Coadministration of one of the present compounds with another bioactive agent as otherwise described herein, often an additional anti-MRSA agent (i.e. an agent which can be used to treat MRSA—such agents may also be used to treat MSSA), will often result in a synergistic enhancement of the activity of the other agent, an unexpected result. One or more of the present compounds may also be coadministered with another bioactive agent (e.g., an antibiotic, antiviral agent, antihyperproliferative disease agent, agents which treat inflammation, including chronic inflammatory disease, among others or as otherwise described herein), depending upon the desired therapeutic outcome and the disease state or condition treated.

"Hydrocarbon" or "hydrocarbyl" refers to any radical containing carbon and hydrogen, which may be straight, branch-chained or cyclic in nature. Hydrocarbons include linear, branched and cyclic hydrocarbons, including alkyl groups, alkylene groups and unsaturated hydrocarbon groups, which may be optionally substituted. Hydrocarbyl groups may be fully saturated or unsaturated, containing one or more double ("ene") or triple ("yne") bonds.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Other terms used to indicate substitutent groups in compounds according to the present invention are as conventionally used in the art. Thus, the term alkylene aryl includes alkylene phenyl such as a benzyl group or ethylene phenyl group, alkylaryl, includes alkylphenyl such a phenyl group which has alkyl groups as substituents, etc. The bond ===== , when used in chemical structures of the present application refers to a single chemical bond, which may be an optional double bond, in context.

The term "additional bioactive agent" including an "additional anti-MRSA agent" is used to describe a drug or other bioactive agent which itself is useful in the treatment of bacterial infections, including Staphylococcus aureus infections, especially including MRSA and is other than a GPER modulator useful in the treatment of bacterial infections, including Staphylococcus aureus, especially including MRSA infections as described herein. These additional bioactive agents may be used to treat disease states and conditions which are commonly found in patients who also have Staphylococcus aureus infections, especially MRSA infections. These additional bioactive agents, include antibiotics, essential oils and alternative therapies such as garlic as otherwise described herein which may be useful for the treatment of bacterial pathogens. In particular, antibiotics and other bioactive agents, including essential oils may be included in compositions and co-administered along with the GPER modulators according to the present invention. Preferred bioactive agents for the treatment of MRSA include, for example, oritavancin (Orbactiv), dalvavancin (Dalvance), tedizolid phosphate, (Sivextro), clindamycin, linezolid (Zyvox), mupirocin (Bactroban), trimethoprim, sulfamethoxazole, trimethoprim-sulfamethoxazole (Septra or Bactrim), tetracyclines (e.g., doxycycline, minocycline), vancomycin, daptomycin, fluoroquinolines (e.g. ciprofloxacin, levofloxacin), macrolides (e.g. erythromycin, clarithromycin, azithromycine) or mixtures thereof. In addition to antibiotics, alternative therapies may be used in combination with the GPER modulators pursuant to the present invention and include the use of manuka honey and/or essential oils such as tea tree oil, oregano oil, thyme, clove, cinnamon, cinnamon bark, eucalyptus, rosemary, lemongrass, geranium, lavender, nutmeg and mixtures thereof.

Antibiotics which are useful in the treatment of Staphylococcus aureus infections (both MSSA and MRSA) depend upon the tissue where the infection is found and whether the Staphylococcus aureus infection is MSSA or MRSA. In general, antibiotics which are found useful in the treatment of general MSSA infections include, for example, β-lactams, oxacillin, nafcillin and cefazolin, which are often used. For general MRSA infections, vancomycin, daptomycin, linezolid, Quinupristin/dalfopristin, Cotrimoxazole, Ceftaroline and Telavancin are more often used.

For treatment of Staphylococcus aureus infections of the heart or its valves (Endocarditis) oxacillin, cefazolin, nafcillin or gentamycin are used for methicillin sensitive strains (MSSA). For MRSA infections of the heart or its valves, useful antibiotics include ciprofloxacin, rifampin, vancomycin and daptomycin as preferred agents.

For Staphylococcus aureus infections of soft tissues and skin—the primary treatment using antibiotics for MSSA includes Cephalexin, Dicloxacillin, Clindamycin and Amoxicillin/clavulanate. For MRSA infections, the preferred antibiotics include Cotrimoxazole, Clindamycin, tetracyclines, Doxycycline, Minocycline and Linezolide, although others may be used.

For skin infections local application of antibiotics like Mupirocin 2% ointment are generally prescribed.

For lung infections or pneumonia—for MRSA cases Linezolid, Vancomycin and Clindamycin are preferred.

For bone and joint infections—for MSSA oxacillin, cefazolin, nafcillin and gentamycin are often used. For MRSA infections, Linezolid, Vancomycin, Clindamycin, Daptomycin and Coptrimoxazole are often used.

For infections of the brain and meanings infection (meningitis)—for MSSA oxacillin, cefazolin, nafcillin, and gentamycin are preferred. For MRSA infections, Linezolid, Vancomycin, Clindamycin, Daptomycin and Cotrimoxazole may be used.

For Toxic Shock Syndrome—for MSSA oxacillin, nafcillin and clindamycin are often used. For MRSA infections Linezolid, Vancomycin and Clindamycin are often used.

Each of the above antibiotics may be combined in methods of the present invention for treating bacterial pathogens, especially Staphylococcus aureus infections (MSSA or MRSA). In addition, one or more of these antibiotics may be combined with one or GPER modulators in pharmaceutical compositions for the treatment of bacterial pathogens, especially Staphylococcus aureus infections (MSSA or MRSA).

"Aryl" refers to a substituted or unsubstituted monovalent aromatic radical having a single ring (e.g., benzene) or multiple condensed rings (e.g., naphthyl, anthracenyl, phenanthryl) and can be can be bound to compound according to the present invention at any position on the ring(s). Other examples of aryl groups include heterocyclic aromatic ring sys-terms "heteroaryl" having one or more nitrogen, oxygen, or sulfur atoms in the ring, such as imidazole, furyl, pyrrole, pyridyl, indole and fused ring systems, among others, which may be substituted or unsubstituted.

"Alkoxy" as used herein refers to an alkyl group bound through an ether linkage; that is, an "alkoxy" group may be represented as —O-alkyl where alkyl is as defined above.

The term "cyclic" shall refer to a carbocyclic or heterocyclic group, preferably a 5- or 6-membered ring, but may include 4 and 7-membered rings. "Bicyclic" or "bicyclo" refers to bicyclic The term "heterocycle" or "heterocyclic" shall mean an optionally substituted moiety which is cyclic and contains at least one atom other than a carbon atom, such as a nitrogen, sulfur, oxygen or other atom. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated. In instances where a heterocyclic ring is fully unsaturated, there is overlap with the term "heteroaryl".

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or halogen (fluoro) group, among others), preferably an alkyl (generally, no greater than about 12 carbon units in length), an optionally substituted aryl (which also may be heteroaryl and may include an alkylenearyl or alkyleneheteroaryl), an optionally substituted heterocycle (especially including an alkyleneheterocycle), $CF_3$, halogen (especially fluoro), thiol, hydroxyl, carboxyl, oxygen (to form a keto group), $C_1$-$C_8$ alkoxy, CN, nitro, an optionally substituted amine (e.g. an alkyleneamine or a $C_1$-$C_6$ monoalkyl or dialkyl amine), $C_1$-$C_8$ acyl, $C_1$-$C_8$ alkylester, $C_1$-$C_8$ alkyleneacyl (keto), $C_1$-$C_8$ alkylene ester, carboxylic acid, alkylene carboxylic acid, $C_1$-$C_8$ thioester, $C_2$-$C_8$ ether, $C_1$-$C_8$ thioether, amide (amido or carboxamido), substituted amide (especially mono- or di-alkylamide) or alkyleneamine, an optionally substituted carbamate or urethane group, wherein an alkylene group or other carbon group not otherwise specified contains from 1 to 8 carbon units long (alternatively, about 2-6 carbon units long) and the alkyl group on an ester group is from 1 to 8 carbon units long, preferably up to 4 carbon units long. Various optionally substituted moieties may be substituted with 5 or more substituents, preferably no more than 3 substituents and preferably from 1 to 3 substituents.

The term "geometric isomer" shall be used to signify an isomer of a compound according to the present invention wherein a chemical group or atom occupies different spatial positions in relation to double bonds or in saturated ring systems having at least three members in the ring as well as in certain coordination compounds. Thus "cis" and "trans" isomers are geometric isomers as well as isomers of for example, cyclohexane and other cyclic systems. In the present invention all geometric isomers as mixtures (impure) or pure isomers are contemplated by the present invention. In preferred aspects, the present invention is directed to pure geometric isomers.

The term "optical isomer" is used to describe either of two kinds of optically active 3-dimensional isomers (stereoisomers). One kind is represented by mirror-image structures called enantiomers, which result from the presence of one or more asymmetric carbon atoms. The other kind is exemplified by diastereomers, which are not mirror images and which contain at least two asymmetric carbon atoms. Thus, such compounds have $2_n$ optical isomers, where n is the number of asymmetric carbon atoms. In the present invention all optical isomers in impure (i.e., as mixtures) or pure or substantially pure form (such as enantiomerically enriched or as separated diastereomers) are contemplated by the present invention. In certain aspects, the pure enantiomer or diastereomer is the preferred compound.

The present invention includes the compositions comprising the pharmaceutically acceptable salt. i.e., the acid or base addition salts of compounds of the present invention and their derivatives. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

Regardless of the mechanism, the compounds of the present invention may be used to treat bacterial infections, often *Staphylococcus aureus* infections, often MRSA and related disease states and/or conditions in patients or subjects who suffer from those conditions or disease states or are at risk for those conditions. In this method a compound in an effective amount is administered to a patient in need of therapy to treat the condition(s) or disease state(s). These disease states and conditions include obesity and diabetes and related disease states and conditions which occur associated with these conditions, such as insulin resistance, metabolic syndrome and the like.

Compositions according to the present invention may be administered by any conventional means known in the art. Pharmaceutical formulations include those suitable for oral, rectal, nasal, topical (including buccal and sub-lingual), vaginal or parenteral (including intramuscular, sub-cutaneous and intravenous) administration. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

In the pharmaceutical aspect according to the present invention, the compound(s) according to the present invention is formulated preferably in admixture with a pharmaceutically acceptable carrier. In general, it is preferable to administer the pharmaceutical composition orally, but certain formulations may be preferably administered parenterally and in particular, in intravenous or intramuscular dosage form, as well as via other parenteral routes, such as transdermal, buccal, subcutaneous, suppository or other route, including via inhalation intranasally. Oral dosage forms are preferably administered in tablet or capsule (preferably, hard or soft gelatin) form. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity.

Compositions suitable for parenteral injection may comprise physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame seed oil, glycerol, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active.

Dosage forms for topical administration include ointments, powders, sprays and inhalants. The compound(s) are admixed under sterile conditions with a physiologically acceptable carrier, and any preservatives, buffers, and/or propellants that may be required. Ophthalmic formulations, eye ointments, powders, and solutions are also contemplated as being within the scope of this invention.

The amount of compound of the instant invention that may be combined with the carrier materials to produce a single dosage form will vary depending upon the host treated, the particular mode of administration. Preferably, the compositions should be formulated so that a dosage of between about 0.001 and 150, preferably about 0.1 to about 50 or about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free compounds and/or pro-drug forms of the compounds according to the present invention.

Chemical Synthesis

The general procedure for preparation of preferred derivatives according to the present invention is set forth in U.S. Pat. No. 7,875,721 which is incorporated by reference in its entirety herein.

EXAMPLES

Example 1

Figure 1:
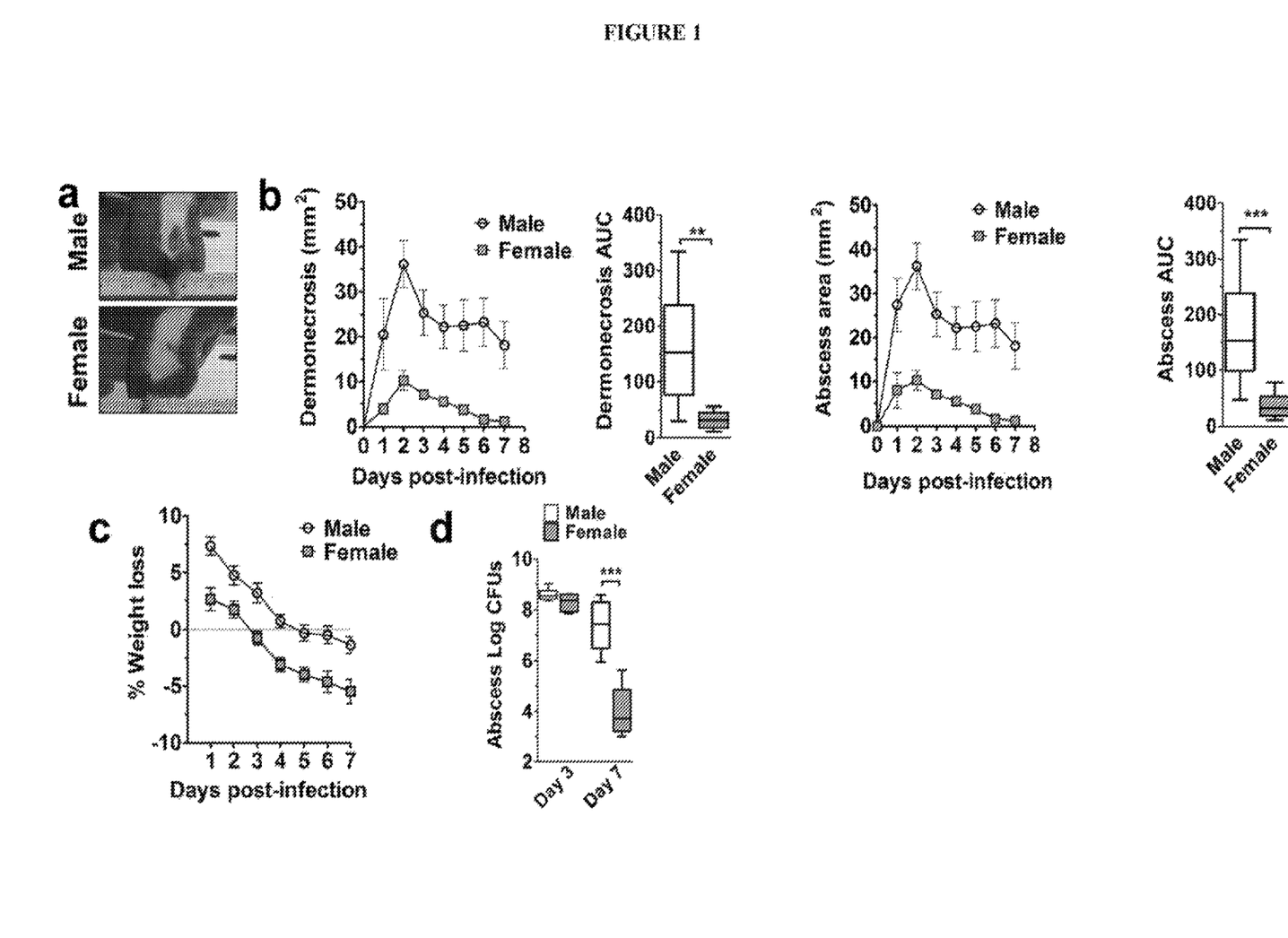
FIG. 1 (*a-d*) shows that *S. aureus* (MRSA USA300 LAC) skin infection is innately limited in female C57BL6 mice compared to males.
Figure 2:
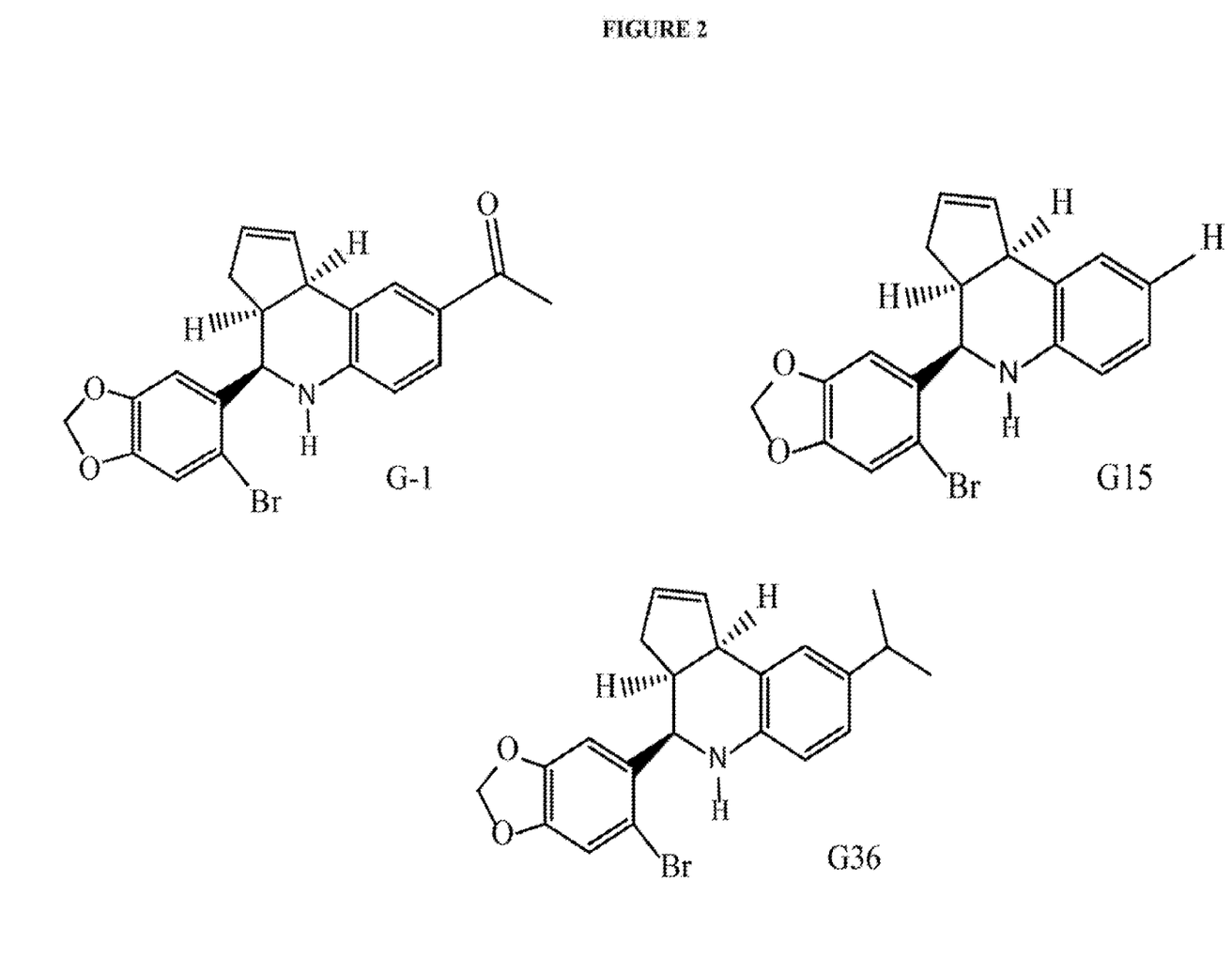
FIG. 2 shows preferred compounds G-1 (GPER agonist) and G15 and G36 (GPER antagonists).

The inventors found that female mice are innately resistance to *S. aureus* skin infection. Compared to males, females infected subcutaneously showed reduced pathogenesis (dermonecrosis, abscess size and weight loss) compared to males. Given these findings, the inventors tried to determine whether activation of the non-canonical estrogen receptor GPER would support an innate defense against *S. aureus* SSTI. FIG. 1 shows that *S. aureus* (MRSA USA300 LAC) skin infection is innately limited in female C57BL/6 mice compared to males.

In a first experiment, male mice were treated one time daily with G1 (10 µg/kg) on days −2 through day +2 relative to infection. These mice were protected against & *aureus*-mediated dermonecrosis through day 7 post-infection. FIG. 3 shows that GPER agonists such as compound G1 inhibits MRSA skin infection from *S. aureus* (MRSA USA300 LAC) skin infection in males.

Accordingly, the results presented in FIG. 3 provides evidence of the activity of GPER modulators in the treatment of MRSA.

Example 2

Figure 7:
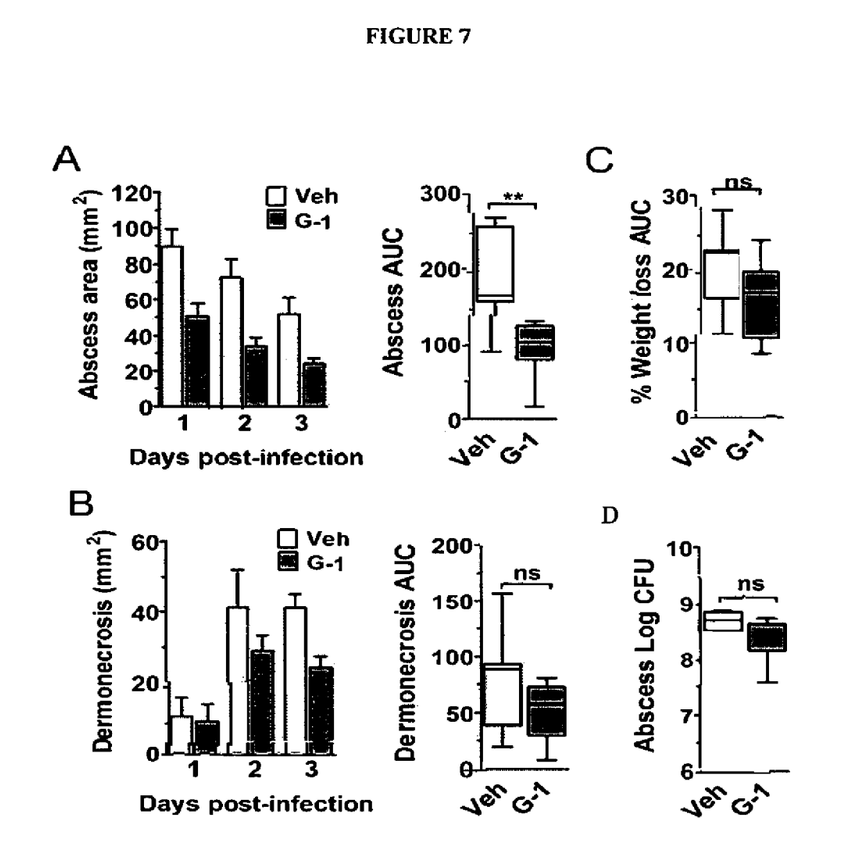
Figure 8:
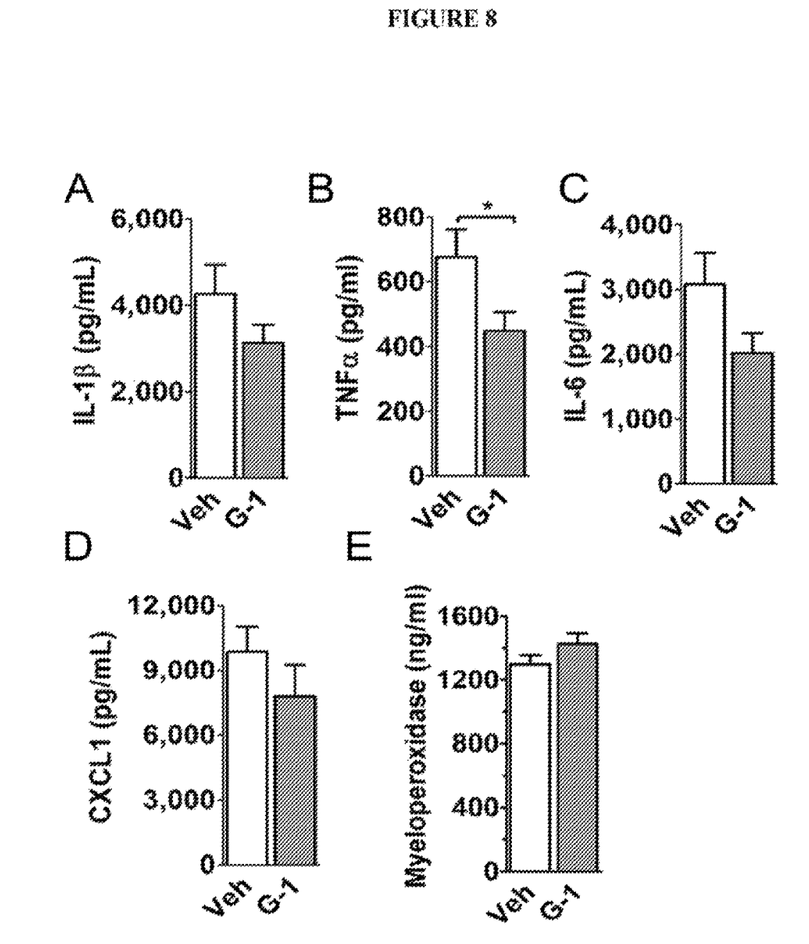
FIG. 8 shows that GPER activation is accompanied by reduced inflammation during SA SSTI in female mice. WT (C57BL/6) female mice were treated i.p. with vehicle or 200 ng G-1 on days −2, −1, 0, +1 and +2 relative to subcutaneous infection with 2.3×10$^7$ CFU of USA300 MRSA isolate LAC. (A) IL-1β, (B) TNFα, (C) IL-6, (D) CXCL1 (n=7-8 mice per group) and (E) myeloperoxidase levels (n=4 mice per group) measured in clarified infection site homogenate collected on day 3 post-infection. Data are mean±sem. *p<0.05; **p<0.01.

In this series of experiments, the inventors used an established mouse model of *Staphylococcus aureus* dermonecrosis (1) to determine the utility of G-1-mediated GPER activation to protect against *S. aureus* SSTI. C57BL/6 male mice were treated with G-1 (2) and infected subcutaneously with the highly virulent MRSA isolate USA300 LAC (3). G-1-treated male mice showed reduced pathogenesis (abscess area, dermonecrosis and weight loss) (FIG. 3A-C), greater bacterial clearance (FIG. 3D). Similarly, G-1 administration was protective in female mice (FIGS. 7 & 8).

Figure 5:
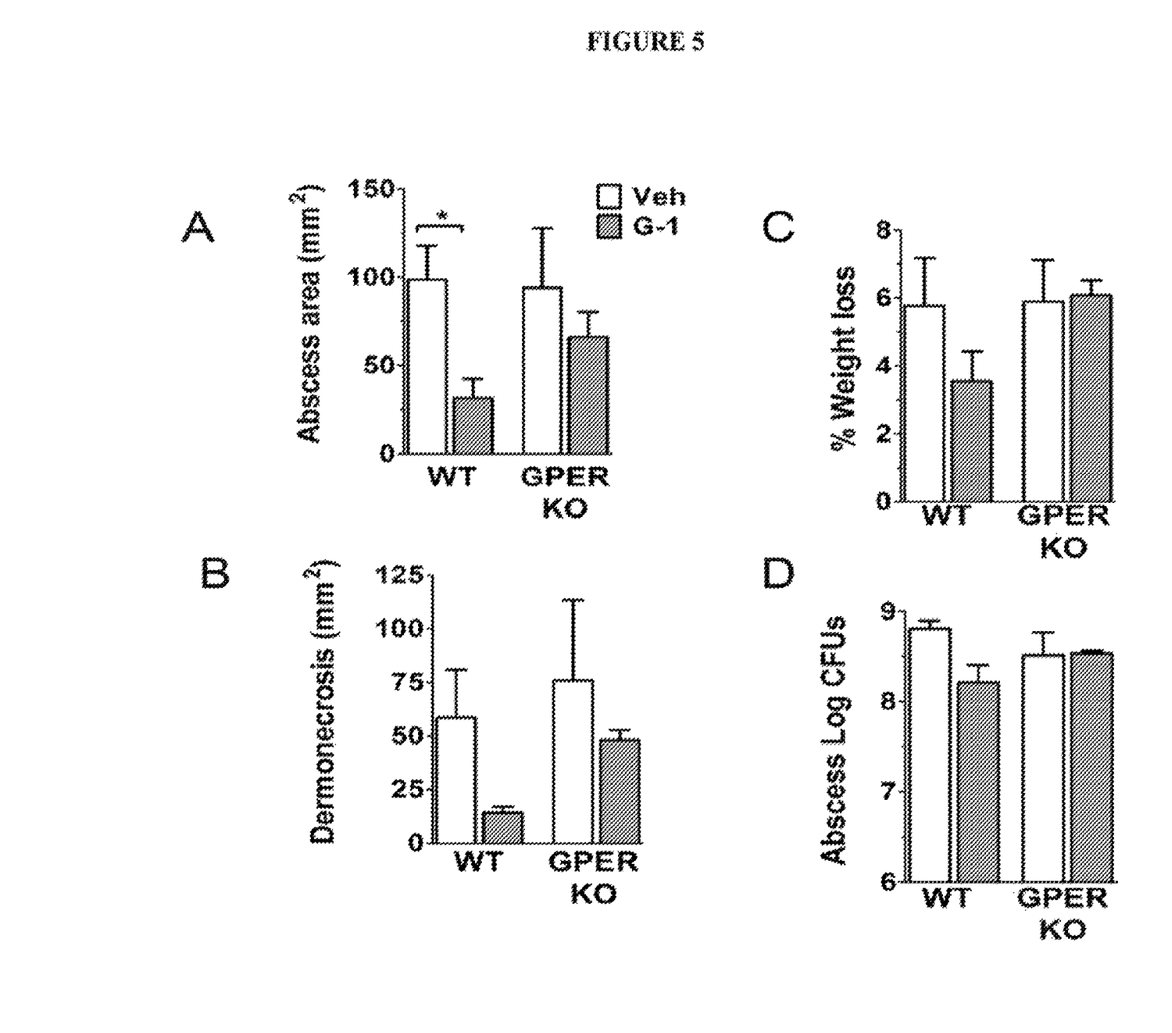
FIG. 5 shows that G-1-mediated protection against SSTI is GPER-dependent. WT (C57BL/6) and GPER KO (on a C57BL/6 background) male mice were treated i.p. with vehicle or 200 ng G-1 on days −2, −1, 0, +1 and +2 relative to subcutaneous infection with $3 \times 10^7$ CFU of USA300 MRSA isolate LAC. Day 3 post-infection (A) abscess area, (B) dermonecrosis, (C) percent weight loss, and well as (D) day 3 post-infection bacterial burden at the site of infection. n=3-5 mice per group.

The efficacy of G-1 in limiting *S. aureus* SSTI is GPER-dependent, as administration of G-1 to GPER knockout mice showed no protective benefit (FIG. 5). This suggests that GPER activation has significant host benefits for innate defense against *S. aureus* SSTI.

Figure 6:
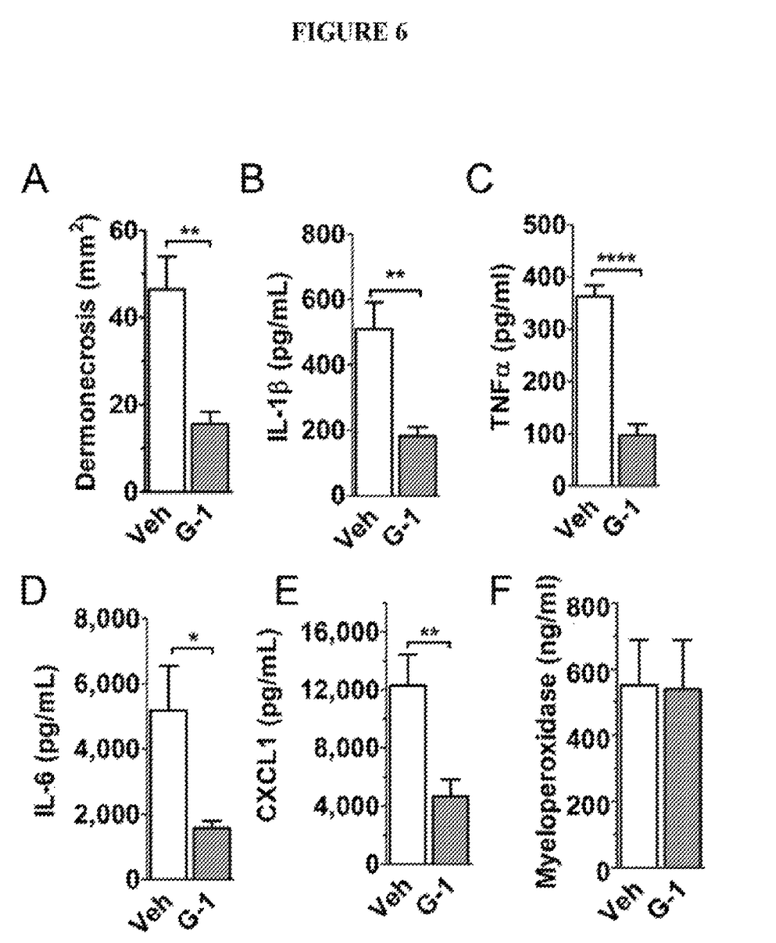
FIG. 6 shows that GPER activation reduces dermonecrosis and inflammation during challenge with HIa. WT (C57BL/6) male mice were treated i.p. with vehicle or 200 ng G-1 on days −2, −1, 0, +1 and +2 relative to subcutaneous injection with 1 µg HIa. (A) Area of dermonecrosis on day 3 post-injection. (B) IL-13, (C) TNFα, (D) IL-6, (E) CXCL1 and (F) myeloperoxidase levels measured in clarified infection site homogenate collected on day 3 post-injection. Data are mean±sem from n=8 mice per group from two independent experiments. *$p<0.05$; $p<0.01$; **$p<0.0001$.

*S. aureus* alpha-hemolysin, also known as alpha-toxin or HIa, is the virulence factor driving dermonecrosis in the mouse skin infection model (1, 4), but also contributes to numerous other *S. aureus* infections (reviewed in (5)). Importantly, G-1 mediated GPER activation significantly reduced dermonecrosis (FIG. 6A) and pro-inflammatory cytokine production (FIG. 6B-E) in mice challenged with purified toxin, suggesting that G-1 could be efficacious against a range of infection types.

1. Malachowa N, Kobayashi S D, Braughton K R, DeLeo F R. Mouse model of *Staphylococcus aureus* skin infection. Methods Mol Biol. 2013; 1031:109-16. doi: 10.1007/978-1-62703-481-4_14. PubMed PMID: 23824894.
2. Bologa C G, Revankar C M, Young S M, Edwards B S, Arterburn J B, Kiselyov A S, Parker M A, Tkachenko S E, Savchuck N P, Sklar L A, Oprea T I, Prossnitz E R. Virtual and biomolecular screening converge on a selective agonist for GPR30. Nat Chem Biol. 2006; 2(4):207-12. doi: 10.1038/nchembio775. PubMed PMID: 16520733.
3. Public health dispatch: outbreaks of community-associated methicillin-resistant *Staphylococcus aureus* skin infections—Los Angeles County, Calif., 2002-2003. Can Commun Dis Rep. 2003; 29(12):110-2. Epub 2003/06/26. PubMed PMID: 12822295.
4. Kennedy A D, Bubeck Wardenburg J, Gardner D J, Long D, Whitney A R, Braughton K R, Schneewind O, DeLeo F R. Targeting of alpha-hemolysin by active or passive immunization decreases severity of USA300 skin infection in a mouse model. J Infect Dis. 2010; 202(7):1050-8. doi: 10.1086/656043. PubMed PMID: 20726702; PMCID: 2945289.
5. Berube B J, Wardenburg J B. *Staphylococcus aureus* alpha-Toxin: Nearly a Century of Intrigue. Toxins (Basel). 2013; 5(6):1140-66. doi: DOI 10.3390/toxins5061140. PubMed PMID: WOS:000320770400006.

The invention claimed is:

1. A method of inhibiting, treating or reducing the likelihood of a *S. aureus* infection in a patient in need comprising administering to said patient an effective amount of at least one G protein-Coupled Estrogen Receptor (GPER) modulator according to the chemical structure:

Where R is an acetyl group, H or an isopropyl group, or a pharmaceutically acceptable salt thereof.

2. The method according to claim 1 wherein said infection is a *S. aureus* infection in a male or female patient and R is an acetyl group.

3. The method according to claim 1 wherein R is an isopropyl group.

4. The method according to claim 1 wherein said infection is a *S. aureus* infection, said patient is a female patient and R is H or isopropyl.

5. The method according to claim 1 wherein R is H.

6. The method according to claim 1 wherein said GPER modulator is co-administered with a selective estrogen receptor modulator (SERM), a selective estrogen receptor degrader or downregulator (SERD), a phytoestrogen or estrogen or a mixture thereof.

7. The method according to claim 6 wherein said SERM is bazedoxifene, broparestrol, clomifene, cyclofenil, lasofoxifene, ormeloxifene, ospemifene, raloxifene, tamoxifen, toremifene, acolbifene (4-hydroxytamoxifen), arzoxifene, brilanestrant, clomifenoxide (clomifene N-oxide), droloxifene (3-hydroxytamoxifen), elascestrant, endomifene, 4-hydroxyetacstil (GW-7604), miproxifene, nafoxidine, nitromifene (CI-628), panomifene, pipendoxifene, tesmilifene, trioxifene, zindoxifene (D-16726), zuclomifene or a mixture thereof.

8. The method according to claim 1 wherein said patient is a human patient.

9. The method according to claim 1 wherein said *S. aureus* infection is MSSA.

10. The method according to claim 1 wherein said *S. aureus* infection is MRSA.

11. The method according to claim 1 wherein said GPER modulator is co-administered with at least one additional bioactive agent selected from the group consisting of an antibiotic, an anticancer agent, and an anti-inflammatory agent.

12. The method according to claim 11 wherein said *S. aureus* infection is MRSA and said antibiotic is an additional anti-MRSA agent.

13. The method according to claim 12 wherein said additional anti-MRSA agent is oritavancin, dalvavancin, tedizolid phosphate, clindamycin, linezolid, mupirocin, trimethoprim, sulfamethoxazole, trimethoprim-sulfamethoxazole, a tetracycline, vancomycin, daptomycin, a fluoroquinoline, a macrolide or a mixture thereof.

* * * * *